United States Patent [19]

Wallace

[11] 4,341,518
[45] Jul. 27, 1982

[54] DENTAL HANDPIECE

[76] Inventor: Richard A. Wallace, Box 201, Gwynedd, Pa. 19436

[21] Appl. No.: 105,595

[22] Filed: Dec. 20, 1979

[51] Int. Cl.³ ............................................. A61C 00/00
[52] U.S. Cl. ........................................ 433/29; 433/82
[58] Field of Search ...................... 433/29, 82; 362/31, 362/32, 96, 89, 91; 350/96.24, 96.26; 128/23

[56] References Cited

U.S. PATENT DOCUMENTS

| | | | |
|---|---|---|---|
| 3,397,457 | 8/1968 | Gosselin | 433/29 |
| 3,614,414 | 10/1971 | Gores | 433/29 |
| 3,893,242 | 7/1975 | Lieb et al. | 433/29 |
| 3,897,134 | 7/1975 | Scrivo et al. | 433/29 |
| 4,020,556 | 5/1977 | Sotman | 433/29 |

*Primary Examiner*—Robert Peshock
*Attorney, Agent, or Firm*—Rene A. Kuypers

[57] ABSTRACT

An air driven dental handpiece is disclosed for rotating a bur in an angled housing that utilizes an arrangement of cooling water, chip air, and light services which are configured at their terminus into a form resembling a human eye. These services are integrated into an oval shape which is totally contained within the handle structure of the handpiece, and exit from the handle immediately adjacent the housing.

In the handpiece, light is transmitted by optic fibers that are enclosed within a rigid, metallic sheath. Light is provided by a flexible fiber optic which abuts the entrance face of the handpiece sheath in a readily detachable, threaded coupling. A spring in the coupling presses the cable fibers firmly against the sheath fibers for maximum light transmission, and also holds the cable securely in the coupling.

A flexible, multi-cavity supply hose includes four cavities which provide the five services of turbine air, turbine exhaust, water, chip air, and light. The fiber optic cable is contained in the exhaust cavity and is connected to a light source. The fiber optic cable can be readily detached from the coupling independent of the supply hose. The turbine air, water, and chip air services of the supply hose are connected within a control console. The exhaust air cavity is terminated at the light source when the source is separate from the control console, and within the control console when the light source is integral with the console.

13 Claims, 22 Drawing Figures

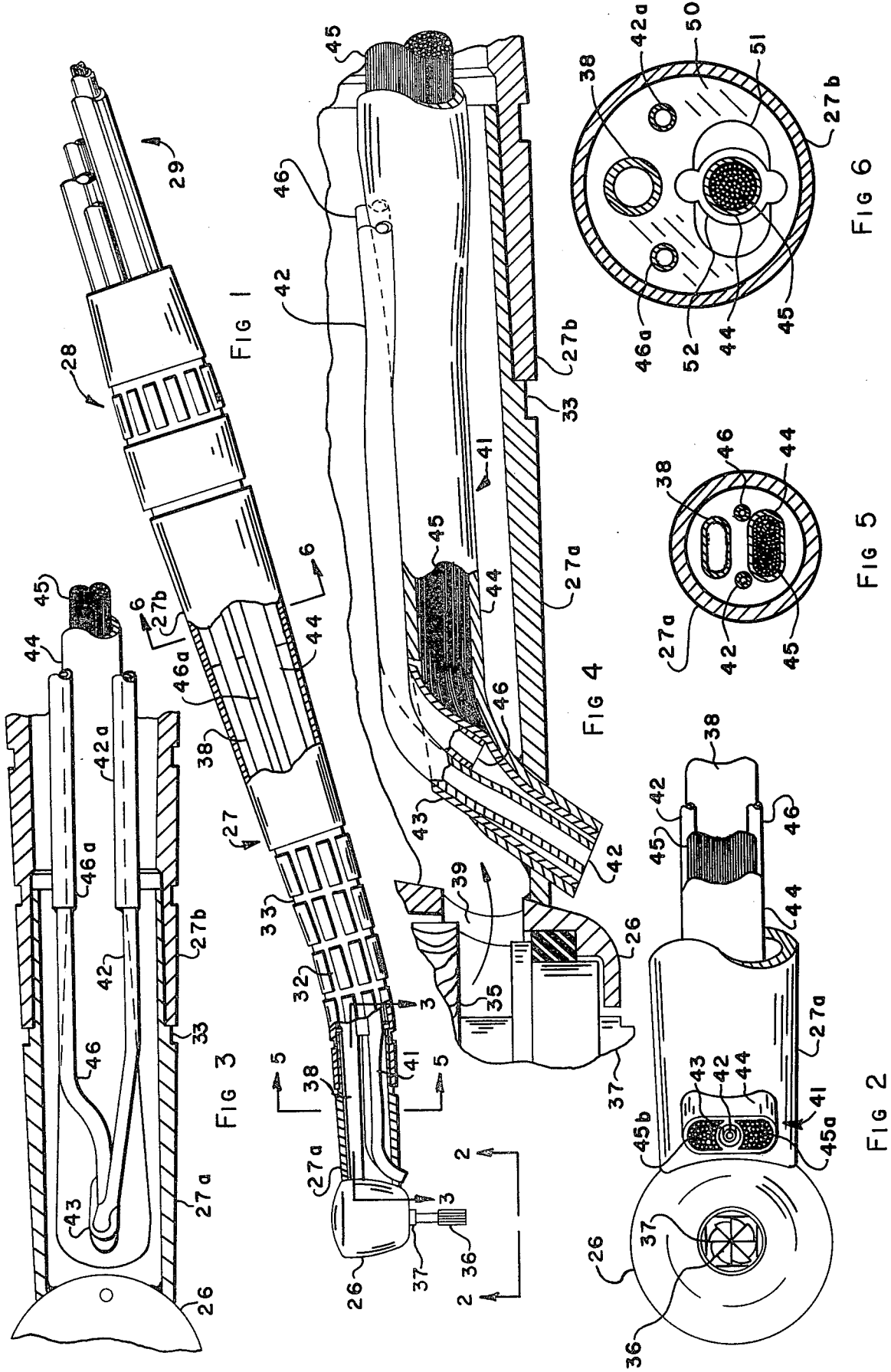

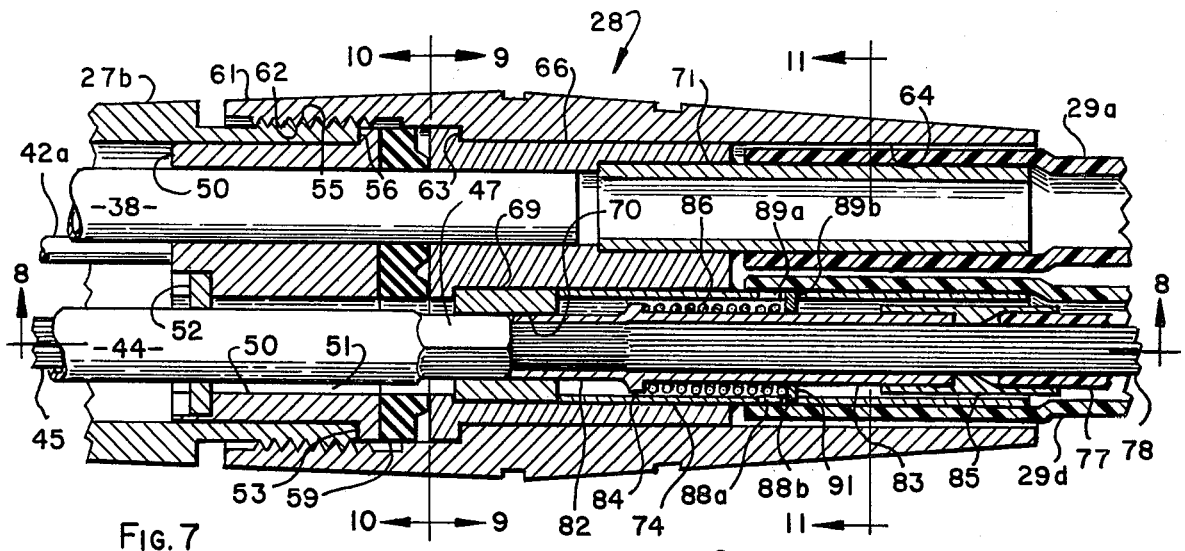
FIG. 7
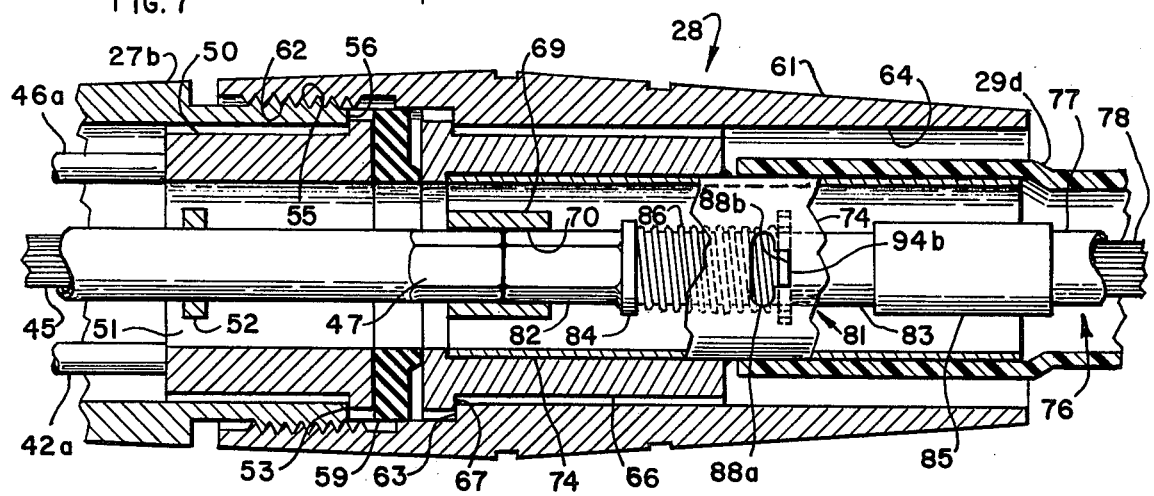
FIG. 8
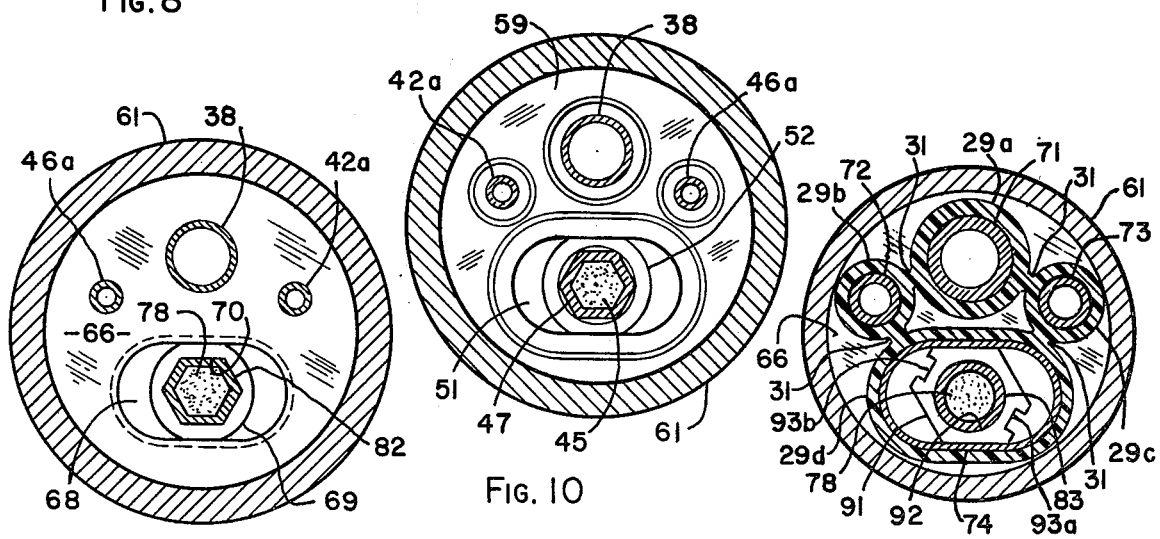
FIG. 9
FIG. 10
FIG. 11

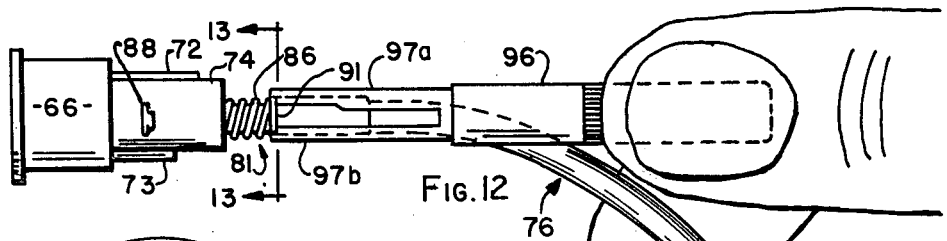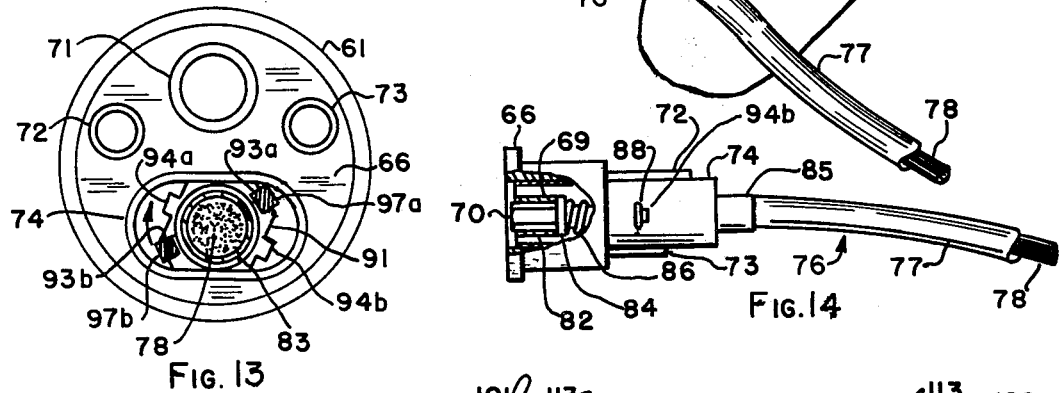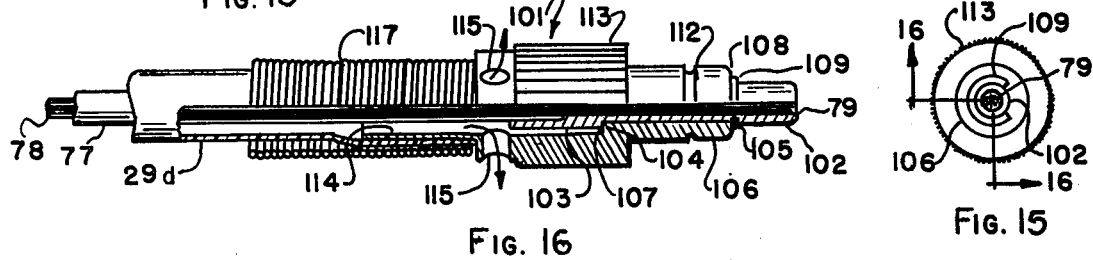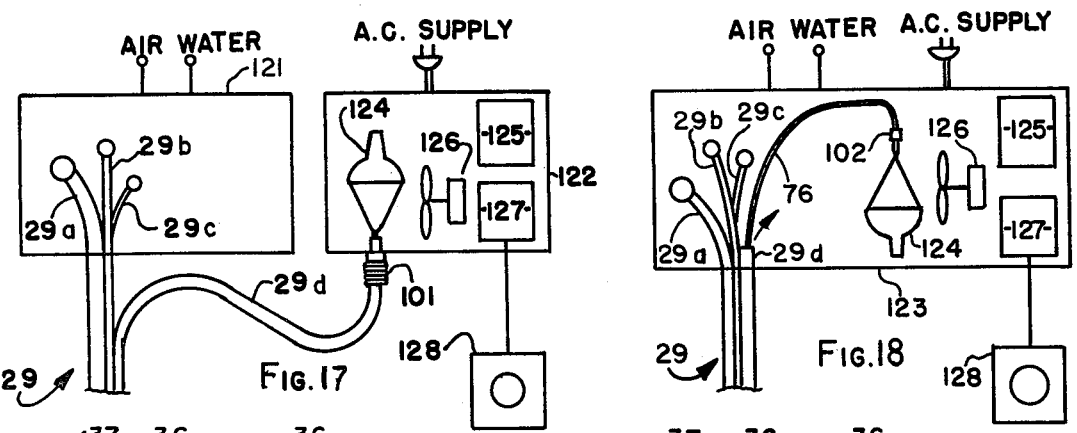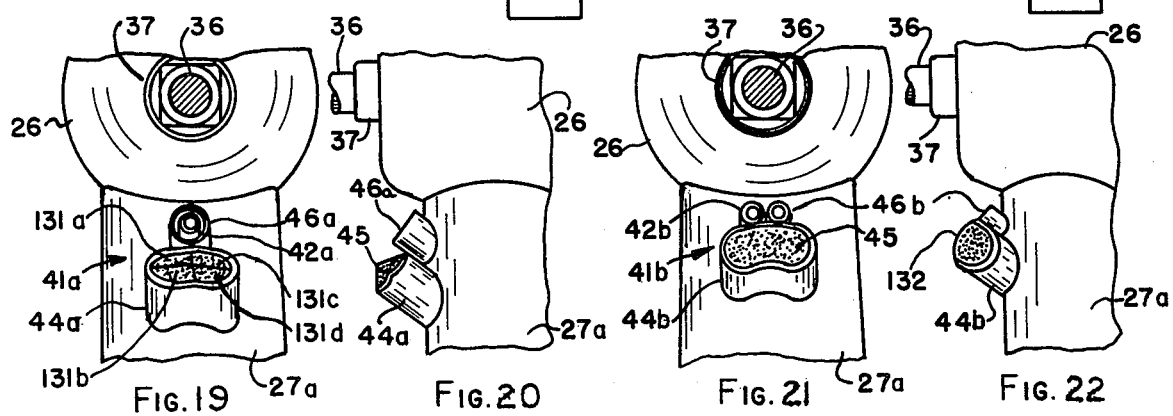

DENTAL HANDPIECE

BACKGROUND OF THE INVENTION

1. Field of the Invention

This invention relates to the field of high speed dental handpieces, and in particular to the field of dental handpieces which utilize an optical system for transmitting light to a bur driven by the handpiece.

2. Description of the Prior Art

In present day dental technology it is generally a practice to utilize overhead lights to illuminate a patient's mouth. Overhead illumination is not entirely satisfactory since it is a compromise between sufficient light for the dentist to work by, but not strong enough to be uncomfortable to the patient. Furthermore, overhead illumination must be aimed to strike the oral cavity, and tends to create shadows and bright spots making restorative procedures tedious and visually fatiguing.

An improved method of illuminating the oral cavity utilizes a dental handpiece which carries its own illumination. Known prior art which teaches this modern technique of dental handpiece illumination are: U.S. Pat. Nos. 3,397,457; 3,638,013; 3,758,951; 3,893,242; and 3,897,134.

U.S. Pat. No. 3,397,457 shows how a regular dental handpiece may be modified for carrying illumination to the patient's mouth by means of a fiber optic light system. Illumination is brought to the handpiece from a light source through a separate fiber optic cable which enters the coupling, runs through the handpiece, emerges on the underside of the neck, and ends immediately adjacent the housing. A recognized shortcoming of this arrangement is that shadows may be generated from the single point of light. The fiber optics below the neck bulk the handpiece at this critical point which limits access, increases work effort, and decreases patient comfort. The separate fiber optic cable running along side the supply hose is also awkward.

In U.S. Pat. No. 3,758,951 a fiber optic illumination system is provided which modifies a regular dental handpiece to carry light to the oral cavity. This is accomplished by routing a fiber optic cable from a light source to the handpiece through a center opening in a special shaped supply hose. At the handpiece the fiber optics are completely independent and external of the coupling and the handle and are taped onto the handpiece. Shortcomings of this arrangement include the increased bulk of the external fiber optics at the handpiece, the lack of easy separation of the fiber optics when the coupling is opened, and the bulky supply hose. In addition, immediately adjacent the coupling the fiber optic cable must emerge from the center of the supply hose to run alongside the handpiece. The entire arrangement is awkward and unappealing in appearance.

Although this patent illustrates a four-conduit supply hose to provide the services of turbine air, water, and chip-air and light a total of five conduits would be needed if turbine exhaust were included. A five conduit supply system unduly complicates the handpiece coupling, adds additional bulk to the supply hose, and makes fabrication of the fiber optic cable difficult and expensive, all of which are undesirable.

In U.S. Pat. No. 3,893,242 a fiber optic dental handpiece is disclosed with a most serious shortcoming. In the handpiece the fiber optic channel is substituted for a chip-air tube, making separate chip-air control impossible. An alternate sample of chip-air is provided by tapping off the turbine air tubes in the handpiece. Another shortcoming of this design is that an elastomeric material is used in the handpiece to provide the spring force needed to press the faces of the fiber optics in the coupling firmly together. Elastomeric and plastic elements in the handpiece are adversely affected by autoclaving. In time the elastomer will lose its resilience and no longer function as an adequate spring. In addition, the optic fibers in the handpiece are constantly flexing. In this design the supply fiber optic cable is cemented into the coupling terminal. This creates a potential problem for replacement of the fiber optic cable since it must have a complete terminal at its distal end.

U.S. Pat. No. 3,897,134 shows a version of a fiber optic dental handpiece which has the fiber optic spring force within the handpiece handle. This shares the problem of U.S. Pat. No. 3,893,242 of being more sensitive to autoclaving, and requiring the fibers in the handpiece to flex.

SUMMARY OF THE INVENTION

The present invention provides a five-service dental handpiece which includes turbine air, turbine exhaust, cooling water, chip-air, and bifurcated light in a novel, compact arrangement that overcomes the bulky designs of the known prior art devices which provide the same services. As is well understood in the dental art, less bulk in the handpiece provides more ease for the dentist and greater comfort to the patient.

The coupling, which connects the five-services from a flexible, multi-conduit supply hose to the handpiece, is of the same standard diameter as couplings providing two, three, or four services. Furthermore, the hose connection through the coupling to the handpiece is arranged to provide the five-services through only four channels. Hence, a four-channel hose required to provide full services to an unlighted handpiece has not had to be expanded to provide the fifth service of light.

It is an additional object of this invention to arrange the multi-conduit supply hose and the fiber optic cable such that air and water services can be supplied from a standard control console and light from a separate light source, or all services can be supplied from a control console combining the air, water, and light sources.

Other objects of this invention will become apparent hereinafter.

DESCRIPTION OF THE DRAWINGS

FIG. 1 is an elevational view, which is partially broken away at two places, of the air driven handpiece and coupling of this invention.

FIG. 2 is an enlarged partial bottom view of FIG. 1.

FIG. 3 is an enlarged sectional partial top view taken along the line 3—3 of FIG. 1.

FIG. 4 is an enlarged sectional elevational view of the distal end of the water-air-light configuration.

FIG. 5 is an enlarged cross sectional view along the lines 5—5 of FIG. 1.

FIG. 6 is an enlarged cross sectional view along the lines 6—6 of FIG. 1.

FIG. 7 is an enlarged sectional elevational view of the proximal end of the handpiece and the handpiece coupling.

FIG. 8 is an enlarged sectional bottom view of the proximal end of the handpiece and the handpiece coupling along the lines 8—8 of FIG. 7.

FIG. 9 is an enlarged cross sectional view of the handpiece coupling along the lines 9—9 of FIG. 7.

FIG. 10 is an enlarged cross sectional view of the proximal end of the handpiece along the lines 10—10 of FIG. 7.

FIG. 11 is an enlarged cross sectional view of the handpiece coupling along the lines 11—11 of FIG. 7.

FIG. 12 is an elevational view of the coupling terminal showing manual insertion of the fiber optic cable using a tool.

FIG. 13 is an enlarged cross sectional view of the coupling terminal along the lines 13—13 of FIG. 12 showing the position of the locking plate upon insertion of the fiber optic cable.

FIG. 14 is an elevational view of the coupling terminal with the fiber optic cable assembled.

FIG. 15 is an end view of the fiber optic cable connector at the light source.

FIG. 16 is an elevational view with partial section along the lines 16—16 of FIG. 15 of the fiber optic cable connector.

FIG. 17 is a schematic diagram of the connection of the five handpiece services to a separate control console and light source.

FIG. 18 is a schematic diagram of the connection of the five handpiece services to a combined control console and light source.

FIG. 19 is an enlarged bottom view of an alternate form of the distal water-air-light configuration having concentric water and chip air services and a faceted light service.

FIG. 20 is an enlarged elevation of the alternate WAL structure shown in FIG. 19.

FIG. 21 is an enlarged bottom view of an alternate form of the distal water-air-light configuration having side-by-side water and chip air services and a dome shaped light service.

FIG. 22 is an enlarged elevation of the alternate WAL structure shown in FIG. 21.

DESCRIPTION OF THE PREFERRED EMBODIMENT

Referring now to FIGS. 1-6, the dental handpiece 25 embodying the invention is shown generally in FIG. 1. It consists of essentially four integrated parts, a housing 26, a handle 27, a coupling 28, and a supply hose 29. Handle 27 is hollow and consists of two sections, a distal handle 27a connecting into the housing 26, and a proximal handle 27b connecting it to the coupling 28. Proximal handle 27b is a hollow, curved, tapered tube having axial grooves 32 and radial grooves 33 on its exterior to form high-friction grip surfaces for an operator's hand. Because the exterior joint between proximal handle 27a and distal handle 27b occurs at a radial groove 33, as shown in FIG. 3, the joint is invisible.

The housing 26 which is mounted at a right angle to distal handle 27a, contains an air driven turbine 35 shown in FIG. 4, for rotating a bur 36 in a shaft 37 (FIGS. 1 and 2). Air for rotating turbine 35 in housing 26 is supplied via a metal tube 38 (FIG. 1). In distal handle 27a, turbine air tube 38 is oval in shape for optimum packaging in this confined space, as shown in FIG. 5; while in proximal handle 27b, tube 38 is round as shown in FIG. 6. After passing through turbine 35, as shown in FIG. 4, the drive air is exhausted along the direction of the arrow through port 39 into the hollow interior of distal handle 27a.

Immediately below and parallel to turbine air tube 38, as shown in elevation in FIG. 1, is assembly 41 which carries cooling water, chip air, and light, hereinafter designated WAL. As seen in side elevation in FIGS. 1 and 4, the WAL assembly 41 is curved at its distal end to impinge water, air, and light at the cutting end of bur 36. Referring now to FIG. 2, an enlarged bottom view of the housing 26, the shaft 37, the bur 36, and the distal handle 27a, the compact, unified exterior configuration of WAL assembly 41 is hown in detail. A small diameter, internal tube 42 carrying water is concentrically surrounded by a larger diameter air nozzle tube 43 supplying chip air. Both water and chip air can be metered by the operator to provide different amounts of cooling and misting between the output end of WAL 41 and the cutting end of bur 36. On opposite sides of the concentric water tube 42 and air nozzle tube 43, encased in fiber optic tube 44, which is ovalled at this point, are glass fiber optic conductors 45a and 45b which supply light in a bifurcated manner. At their output the optic fibers 45a and 45b are potted in epoxy and they and tubes 42, 43, and 44 are cut to the same length, and the fibers polished to give a durable, optically efficient surface.

Referring now to FIG. 4 where the WAL assembly is depicted in enlarged elevation, water tube 42 enters in front of air nozzle tube 43 and then bends back slightly and emerges concentrically with nozzle tube 43 at the output. Chip air is supplied through chip air tube 46 to the top of the nozzle tube 43 and terminates immediately through chip air tube 46 to the top of the nozzle tube 43 and terminates immediately after making a bend. Nozzle tube 43 is ovalled at its top end as shown in FIG. 3, but round at its output as shown in FIG. 2. In fabrication, tubes 42, 43, 44, and 46 are soldered together to make at their output three separate, leakproof passages. The innermost passage conducts water through tube 42, the second tube 43 conducts chip air concentrically around water tube 42, and the third bifurcated passage on opposite sides of tubes 42 and 43, through tube 44 holds glass fibers 45a and 45b which conduct light.

As shown in FIG. 4, immediately behind nozzle tube 43, glass fibers 45 merge and run as a single bundle in fiber optic tube 44. As depicted in enlarged cross section of FIG. 5, tube 44 is ovalled within distal handle 27a. Approximately adjacent the interior junction of distal handle 27a and proximal handle 27b fiber optic tube 44 becomes round in cross section as shown in FIG. 4. Continuing, fiber optic tube 44 curves to conform with the bend in proximal handle 27b, and straightens as it enters the coupling 28 (FIG. 1). Water tube 42 and chip air tube 46 change to larger diameter tubes 42a and 46a respectively in the vicinity of the interior junction of handle sections 27a and 27b as shown in FIG. 3. The arrangement of the four rigid supply tubes: turbine air tube 38, water tube 42, fiber optic tube 44, and chip air tube 46 in the distal handle 27a is shown in cross section in FIG. 5. In FIG. 6 these same four tubes are shown in cross section in the proximal handle 27b. Exhaust air from turbine 35 after passing through the interior of proximal handle 27b passes through plug 50 through oval slot 51, on two sides of fiber optic tube 44. A bridge 52 supports the fiber optic tube 44 at this point to keep it in the center of slot 51 and yet allow free flow of exhaust turbine air to the coupling 28.

The internal structure of the proximal handle 27b, the coupling 23, and the 4-conduit supply hose 29 are shown in FIGS. 7-11. Coupling sleeve 61 has internal threads 62 which engage external threads 55 of proximal handle 27b. Sleeve 61 has an internal annular shoulder 63 and cylindrical section 64. Slidably located in cylindrical section 64 is terminal 66 which forms a connection means to the 4-conduit supply hose 29. Terminal 66 includes a radial flange 67 which abuts shoulder 63, and plug 50 has a radial flange 53 which engages end 56 of proximal handle 27b. Between plug 50 and terminal 66 is an elastomeric gasket 59. When coupling sleeve 61 is threaded onto proximal handle 27b, terminal 66 presses against gasket 59 which in turn presses against plug 50 making a secure, leakproof connection.

As shown in FIG. 10, four metal tubes: turbine air tube 38, water tube 42a, chip air tube 46a, and fiber optic tube 44 extend through plug 50 and gasket 59. These tubes fit into registering apertures in terminal 66. Tubes 38, 42a, and 46a are round at this intersection, but fiber optic tube 44 is formed into a hexagon cross section at its end 47 for efficient light transmission. As at their output, fibers 45 are potted and polished at end 47.

As shown in FIG. 11, terminal 66 has four tubes permanently fastened to it. Turbine air tube 71 is centrally positioned with the smaller water tube 72 and chip air tube 73 symetrically located below and on each side thereof. The tubine exhaust air tube 74 is oval shaped and is located below the water 72 and chip air 73 tubes. The pattern of these four tubes is symetrical about the vertical center line of FIG. 11. A 4-conduit, flexible supply hose 29 is frictionally held onto the four metal tubes. Turbine air tube 71 holds conduit 29a; water tube 72 holds conduit 29b; chip air tube 73 holds conduit 29c, and exhaust tube 74 hold conduit 29d. The four tubes are held together by webs 31 shown in FIG. 11.

The fiber optic supply cable 76 (FIG. 8), composed of a flexible jacket 77 and glass fibers 78, runs inside supply hose exhaust conduit 29d, and within terminal 66, passes along the center line of turbine exhaust tube 74. As shown in FIG. 9, terminal 66 has a slot 68 in it which has the same deminsions as the inside of exhaust tube 74. Held in place by tube 74 is guide 69 which has a round exterior and a hexagon shaped hole 70 in it. Turbine exhaust air flows on two sides of guide 69.

Glass fibers 78 are terminated within coupling 28 in a fiber optic fitting 81 (FIG. 8) which has a hexagon cross section 82 at its output end, a round section 83 at its input end, and a flange 84 between. The hexagon end 82 provides efficient light transmission into matching end 47 of fiber optic tube 44 in handle 27b, and prevents rotation of optic supply cable 76 which avoids scratching of the glass surfaces and attenuation of the light transmitted through the joint. Fibers 78 are potted and polished at their output in hex section 82. Pressed or soldered onto section 83 of the fiber optic fitting 81 is tube 85 into which flexible jacket 77 is adhered. Between flange 84 and tube 85 is compression spring 86 and lock plate 91 (FIG. 7). As shown in FIGS. 11 and 13, lock plate 91 consists of a hole 92, two notches 93a and 93b, and two tabs 94a and 94b. Punched into the top and bottom of exhaust air connector tube 74 (FIGS. 7 and 8) are two T-slots each consisting of two parts. The bottom T-slot consists of an oval section 88a and a rectangular notch 88b, while the top T-slot, identical in shape to the bottom, (FIG. 7) consists of an oval section 89a and a rectangular notch 89b. Within terminal 66 the fiber optic fitting 81 is slidably mounted with hexagon section 82 supported by hexagon hole 70, and round section 83 sliding through hole 92 (FIG. 11) of lock plate 91. Spring 86 (FIGS. 7 and 8) holds lock plate 91 firmly in place by tab 94a fitting into the complementary T-slot notch 89b, and tab 94a fitting into T-slot notch 88b. The opposite end of spring 86 pressing against flange 84 holds supply cable optic fibers 76 firmly against handpiece optic fibers 45.

In FIGS. 12-14 the method of manually connecting the supply fiber optic cable 76 to terminal 66 is shown. A cylindrical insertion wrench 96, held between an operator's thumb and forefinger, has prongs 97a and 97b which are inserted into notches 93a and 93b of lock plate 91. Supply fiber optic cable 76 passes between the prongs 97a and 97b as shown in FIG. 12. Fiber optic fitting 81 is inserted into the oval shaped exhaust air hose connector 74 until hex end 82 (FIG. 14) of fitting 81 engages hex hole 70 in guide 69. When flange 84 of fitting 81 touches guide 69, fitting 81 stops moving. Further insertion of wrench 96 into connector 74 causes spring 86 to compress. As lock plate 91 reaches T-slot oval sections 88a and 89a, wrench 96 is rotating clokwise, in the direction of the arrow of FIG. 13. Relaxing the insertion force on the wrench allows spring 86 to seat lock plate tabs 94a securely in T-slot notches 89b and 88b respectively. Wrench 96 is then withdrawn. FIG. 14 shows supply fiber optic cable 76 assembled to terminal 66. The position of lock plate 91 after assembly is shown in FIG. 11. Lock plate tabes 94a and 94b are flush with the outside surfaces of exhaust air hose connector 74 to allow supply hose 29d to be slipped in place properly. Supply hose 29d also covers T-slot oval sections 88a and 89a to prevent air leakage.

FIGS. 15 and 16 show the structure of the fiber optic fitting 101 at the illumination source. Flexible jacket 77 and optic fibers 78 of supply cable 76 terminate in fitting 101 in a ferrule 102. The end of jacket 77 is adhered to enlarged end 103 of ferrule 102, and fibers 78 are potted and polished at their input end 79. Ferrule 102 fits concentrically through plug 106 and is held in place at one end by flange 104 of ferrule 102 which abuts internal annular ring 107 of plug 106, and at the other end by C-ring 109 which is held in groove 105 of ferrule 102 and abuts end 108 of plug 106. Plug 106 contains detent groove 112 for secure attachment to the illumination source, and knurl 113 to provide a good finger grip surface for attachment and detachment. The turbine exhaust air conduit 29d of supply hose is terminated by slipping it over tubular end 114 of plug 106. Strain relief spring 117 frictionally fits over exhaust air conduit 29d and tubular end 114. Turbine exhaust air flowing through conduit 29d exits to the atmosphere through exhaust holes 115 in plug 106 in the direction of the arrows shown in FIG. 16.

FIGS. 17 and 18 depict schematically the connection of the supply hose 29 to sources of compressed air, water, and light. In FIG. 17 air and water are supplied by a standard control console 121, and light by a separate light source 122. In console 121 turbine air conduit 29a is connected to its appropriate internal source, as is conduit 29b to a source of water, and conduit 29c to a source of chip air. In light source 122 light is supplied from projection lamp 124. Transformer 125 supplies power to the lamp and fan 126 cools it. Lamp brightness is varied by dimmer circuit 127 and remote dimmer control 128. Supply cable 29 is split such that turbine exhaust conduit 29d is separate from and preferable longer than conduits 29a, 29b, and 29c. Both turbine exhaust cable 29d and fiber optic cable 76 terminate in fiber optic fitting 101 which is plugged into light source 122.

In FIG. 18 air, water, and light are supplied by a combined control console and light source 123. Turbine air conduit 29a, water conduit 29b, and chip air conduit 29c are connected to their appropriate internal sources. Light is supplied from projection lamp 124 powered by transformer 125 and cooled by fan 126. Lamp brightness is varied by dimmer circuit 127 and remote dimmer control 128. Exhaust air conduit 29d is terminated within combined console 123, and fiber optic supply cable 76 continues to the front of lamp 124 where it terminates in ferrule 102. Exhaust air flows in the direction of the arrow in FIG. 18 within console 123.

DESCRIPTION OF THE ALTERNATE EMBODIMENT

FIGS. 19 to 22 show two alternate embodiments of the WAL, water-air-light, assembly.

FIG. 19 is an enlarged bottom view and FIG. 20 an elevation of the handpiece showing WAL assembly 41a in which light emerges through optic fibers 45 in oval tube 44a, while water emerges through inner concentric tube 42a and chip air through outer concentric tube 46a, these two tubes being tangent to oval tube 44a and located between oval tube 44a and housing 26. The distal end of oval tube 44a holding optic fibers 45 has been cut into four facets 131a, 131b, 131c and 131d to split the beam of emerging light into four overlapping beams to reduce shadows caused by bur 36.

FIG. 21 is an enlarged bottom view, and FIG. 22 an elevation of the handpiece showing WAL assembly 41b in which light emerges through optic fibers 45 in oval tube 44b, while water emerges through tube 42b and chip air through tube 46b, tubes 42b and 46b being the same diameter and tangent to each other and to oval tube 44b, and also located between oval tube 44b and housing 26. The distal end of oval tube 44b holding optic fibers 45 has been formed into a dome contour 132 to reduce bur 36 shadows.

It is to be understood that the three embodiments of the WAL structure 41, 41a, and 41b can have the distal end of oval tube 44 formed in a variety of ways to reduce bur shadows such that many combinations of flat facets and curved faces can be used with any of the three WAL configurations drawn and described.

I claim:

1. In a contra angle dental handpiece for driving a bur within a head, which is attached to the distal end of a hollow handle, with the proximal end of the handle attached to a coupling, the improvement comprising:
   a. means respectively located wholly within said handle for conducting chip air, water, and light services from said coupling to the distal end, where the services exit together at a single location in a cluster therefrom,
   b. whereby chip air, water and light emerge immediately adjacent the head without adding bulk to the handle, and light emanating from said light service falling on said bur with minimum shadow.

2. The dental handpiece in accordance with claim 1, the additional improvement comprising:
   a. further means for diffusing said light exiting adjacent said housing, whereby shadows caused by said bur are minimized.

3. The handpiece in accordance with claim 1 wherein
   a. said means for conducting light from said coupling is oval shaped at its distal end.

4. The handpiece in accordance with claim 3 which further includes:
   a. Means for enabling said water and chip air to exit concentrically from the distal end of the handle centered within said oval shaped means.

5. The handpiece in accordance with claim 4 which further includes:
   a. Means for enabling said light to exit from the handle on either side of the concentrically arranged water and chip air means, whereby said light is bifurcated in exiting from said handle.

6. The handpiece in accordance with claim 3 which further includes:
   a. Means for enabling said water and chip air to exit concentrically from the handle located between said housing and said oval means.

7. The handpiece in accordance with claim 3 which further includes:
   a. Means for enabling said water and chip air to exit contiguous to each other located between said housing and said oval means.

8. A dental handpiece for driving a bur within a housing which is attached to the distal end of a hollow handle, wherein said handpiece includes services of turbine exhaust and turbine air, water, chip air, and light through optic fibers which are delivered through tubes, the improvement comprising:
   a. a rigid tube enclosing the optic fibers in the handpiece,
   b. wherein said tube is penetrated by a concentric arrangement of water and air tubes at the distal end of the handle wherein all services exit as a group.

9. A dental handpiece which encloses the services of turbine air, water, chip air, light provided by an elongated bundle of light conducting fibers extending through a hollow handle, and turbine exhaust air is released through an opening in a plug located at the proximal end of said handle, the improvement comprising:
   a. passing the fiber optic bundle through the exhaust air opening of said plug.

10. In a dental handpiece having a multi-conduit supply hose with an exhaust air conduit, the improvement comprising:
    a. A fiber optic cable located in the exhaust air conduit, whereby one said conduit carries the two services one of light and a second of exhaust air.

11. A fiber optic light source having a receptacle to receive a pluggable fitting through which light is supplied through a fiber optic cable to an air driven dental handpiece, the improvement comprising:
    a. means to attach to the fitting an exhaust air conduit as well as the fiber optic cable located within the conduit,
    b. means on said fitting to allow turbine air to exhaust to the atmosphere,
    c. whereby the fitting integrally combines a pluggable fiber optic connection to the light source with turbine air exhaust.

12. In a dental handpiece service supply console and light source to which a multi-conduit supply hose including an exhaust conduit and a fiber optic cable, the improvement comprising:

a. The fiber optic cable located within said exhaust conduit, and optically connected to the light source, b. a remote dimmer electrically connected to the light source.

13. In a coupling for a dental handpiece in which light is supplied by a flexible optic cable through a fixed fiber optic bundle in a handle of said handpiece, the improvement comprising:

a. a spring loaded fiber optic fitting located in the coupling for holding said fiber optic cable firmly against the fiber optic bundle when the coupling is closed;

b. a multi-conduit supply hose connected to said coupling and a locking slot formed in its surface;

c. an exhaust air connector tube located in said coupling, d. a lock plate located on the fiber optic fitting in the coupling;

e. spring means positioned between the lock plate and an abutment on the fitting;

d. the lock plate assembled in the locking slot to hold the fiber optic fitting in position in the coupling, e. whereby the fiber optic cable is manually removeable from the coupling independently of the multi-conduit supply hose.

* * * * *